United States Patent
Li et al.

(10) Patent No.: US 10,621,719 B2
(45) Date of Patent: Apr. 14, 2020

(54) SYSTEMS AND METHODS FOR INSPECTING AND EVALUATING QUALITIES OF PRINTED REGIONS ON SUBSTRATES FOR ABSORBENT ARTICLES

(71) Applicant: The Procter & Gamble Company, Cincinnati, OH (US)

(72) Inventors: Wenbin Li, Mason, OH (US); Juergen Dornheim, Frankfurt (DE); Karen Marie Singer, Norwood, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/401,129

(22) Filed: May 2, 2019

(65) Prior Publication Data

US 2019/0340740 A1 Nov. 7, 2019

Related U.S. Application Data

(60) Provisional application No. 62/666,122, filed on May 3, 2018.

(51) Int. Cl.
| | |
|---|---|
| *G06T 7/00* | (2017.01) |
| *A61F 13/84* | (2006.01) |
| *G01N 21/88* | (2006.01) |
| *G06Q 30/02* | (2012.01) |
| *G06T 7/90* | (2017.01) |

(Continued)

(52) U.S. Cl.
CPC .............. *G06T 7/001* (2013.01); *A61F 13/84* (2013.01); *B41F 33/0045* (2013.01); *G01B 11/285* (2013.01); *G01J 3/0275* (2013.01); *G01J 3/463* (2013.01); *G01N 21/8851* (2013.01); *G06Q 30/0201* (2013.01); *G06T 7/90* (2017.01); *H04N 7/181* (2013.01); *A61F 2013/8491* (2013.01);

(Continued)

(58) Field of Classification Search
CPC ...................... G06T 2207/30144; G06T 7/001
See application file for complete search history.

(56) References Cited

U.S. PATENT DOCUMENTS

| | | |
|---|---|---|
| 2,075,189 A | 3/1937 | Galligan et al. |
| 3,025,199 A | 3/1962 | Harwood |

(Continued)

FOREIGN PATENT DOCUMENTS

EP 1528907 B1 9/2008

*Primary Examiner* — Paulos M Natnael
(74) *Attorney, Agent, or Firm* — C. Brant Cook

(57) ABSTRACT

The present disclosure relates to systems and processes for inspecting and evaluating qualities of printed regions on substrates, wherein the systems and methods may be configured to eliminate subjective aspects relating to human involvement in performing visual checks when evaluating print quality. The systems may include one or more communication networks connecting one or more sensors with an analyzer. In operation, ink is applied to a substrate to create at least one printed region, and the sensors are configured to inspect the printed region. The sensors may be configured to communicate measurements and/or images to the analyzer. And the analyzer may then calculate one or more quality subscores based on respective measurements and/or images. In turn, a full print quality score may be calculated based on one or more of the quality subscores. The analyzer may then execute a control action based on the full print quality score.

20 Claims, 6 Drawing Sheets

(51) Int. Cl.
*G01J 3/02* (2006.01)
*G01J 3/46* (2006.01)
*G01B 11/28* (2006.01)
*H04N 7/18* (2006.01)
*B41F 33/00* (2006.01)

(52) U.S. Cl.
CPC ............... A61F 2013/8497 (2013.01); G06T 2207/10024 (2013.01); G06T 2207/30144 (2013.01)

(56) References Cited

U.S. PATENT DOCUMENTS

| | | | |
|---|---|---|---|
| 3,465,350 A | 9/1969 | Keur et al. | |
| 3,465,351 A | 9/1969 | Keur et al. | |
| 3,848,594 A | 11/1974 | Buell | |
| 3,860,003 A | 1/1975 | Buell | |
| 4,107,364 A | 8/1978 | Sisson | |
| 4,209,563 A | 6/1980 | Sisson | |
| 4,324,246 A | 4/1982 | Mullane et al. | |
| 4,342,314 A | 8/1982 | Radel et al. | |
| 4,463,045 A | 7/1984 | Ahr et al. | |
| 4,515,595 A | 5/1985 | Kievit et al. | |
| 4,556,146 A | 12/1985 | Swanson et al. | |
| 4,589,876 A | 5/1986 | Van Tilburg | |
| 4,610,678 A | 9/1986 | Weisman et al. | |
| 4,662,875 A | 5/1987 | Hirotsu et al. | |
| 4,673,402 A | 6/1987 | Weisman et al. | |
| 4,687,478 A | 8/1987 | Van Tilburg | |
| 4,695,278 A | 9/1987 | Lawson | |
| 4,704,115 A | 11/1987 | Buell | |
| 4,795,454 A | 1/1989 | Dragoo | |
| 4,834,735 A | 5/1989 | Alemany et al. | |
| 4,834,741 A | 5/1989 | Sabee | |
| 4,846,815 A | 7/1989 | Scripps | |
| 4,888,231 A | 12/1989 | Angstadt | |
| 4,894,060 A | 1/1990 | Nestegard | |
| 4,909,803 A | 3/1990 | Aziz et al. | |
| 4,940,464 A | 7/1990 | Van Gompel et al. | |
| 4,946,527 A | 8/1990 | Battrell | |
| 4,950,264 A | 8/1990 | Osborn, III | |
| 5,009,653 A | 4/1991 | Osborn, III | |
| 5,092,861 A | 3/1992 | Nomura et al. | |
| 5,151,092 A | 9/1992 | Buell et al. | |
| 5,167,897 A | 12/1992 | Weber et al. | |
| 5,221,274 A | 6/1993 | Buell et al. | |
| 5,246,433 A | 9/1993 | Hasse et al. | |
| 5,267,992 A | 12/1993 | Van Tilburg | |
| 5,286,543 A | 2/1994 | Ungpiyakul et al. | |
| 5,330,458 A | 7/1994 | Buell et al. | |
| 5,359,525 A | 10/1994 | Weyenberg | |
| 5,360,420 A | 11/1994 | Cook et al. | |
| 5,562,646 A | 10/1996 | Goldman et al. | |
| 5,569,234 A | 10/1996 | Buell et al. | |
| 5,599,335 A | 2/1997 | Goldman et al. | |
| 5,628,097 A | 5/1997 | Benson et al. | |
| 5,643,588 A | 7/1997 | Roe et al. | |
| 5,669,894 A | 9/1997 | Goldman et al. | |
| 5,674,216 A | 10/1997 | Buell et al. | |
| 5,702,551 A | 12/1997 | Huber et al. | |
| 5,735,840 A | 4/1998 | Kline et al. | |
| 5,897,545 A | 4/1999 | Kline et al. | |
| 5,916,661 A | 6/1999 | Benson et al. | |
| 5,928,212 A | 7/1999 | Kline et al. | |
| 5,957,908 A | 9/1999 | Kline et al. | |
| 5,968,025 A | 10/1999 | Roe et al. | |
| 6,004,893 A | 12/1999 | Van Tilburg | |
| 6,107,537 A | 8/2000 | Elder et al. | |
| 6,107,539 A | 8/2000 | Palumbo et al. | |
| 6,118,041 A | 9/2000 | Roe et al. | |
| 6,120,487 A | 9/2000 | Ashton | |
| 6,120,489 A | 9/2000 | Johnson et al. | |
| 6,153,209 A | 11/2000 | Vega et al. | |
| 6,251,097 B1 | 6/2001 | Kline et al. | |
| 6,410,129 B2 | 6/2002 | Zhang et al. | |
| 6,426,444 B2 | 6/2002 | Roe et al. | |
| 6,432,098 B1 | 8/2002 | Kline et al. | |
| 6,545,197 B1 | 4/2003 | Muller et al. | |
| 6,586,652 B1 | 7/2003 | Roe et al. | |
| 6,617,016 B2 | 9/2003 | Zhang et al. | |
| 6,627,787 B1 | 9/2003 | Roe et al. | |
| 6,669,618 B2 | 12/2003 | Reising et al. | |
| 6,790,798 B1 | 9/2004 | Suzuki et al. | |
| 6,801,828 B2 | 10/2004 | Popp et al. | |
| 6,811,239 B1 | 11/2004 | Salacz | |
| 6,820,022 B2 * | 11/2004 | Popp | A61F 13/15772 702/81 |
| 6,825,393 B2 | 11/2004 | Roe et al. | |
| 6,861,571 B1 | 3/2005 | Roe et al. | |
| 7,123,981 B2 * | 10/2006 | Dollevoet | A61F 13/15772 700/143 |
| 7,569,039 B2 | 8/2009 | Matsuda et al. | |
| 8,145,343 B2 * | 3/2012 | DeBruler | A61F 13/15772 226/10 |
| 8,145,344 B2 * | 3/2012 | DeBruler | A61F 13/15772 700/125 |
| 8,244,393 B2 | 8/2012 | McLaughlin et al. | |
| 9,211,356 B2 | 12/2015 | Gruenbacher et al. | |
| 9,777,435 B2 * | 10/2017 | Zhou | D21H 17/36 |
| 9,910,429 B2 | 3/2018 | Berg et al. | |
| 2003/0086108 A1 * | 5/2003 | Barkis | G06Q 10/087 358/1.13 |
| 2003/0233082 A1 | 12/2003 | Kline et al. | |
| 2004/0097895 A1 | 5/2004 | Busam et al. | |
| 2004/0158212 A1 | 8/2004 | Ponomarenko et al. | |
| 2005/0107764 A1 | 5/2005 | Matsuda et al. | |
| 2007/0078427 A1 | 4/2007 | Raycheck et al. | |
| 2007/0093769 A1 | 4/2007 | Kline et al. | |
| 2009/0312730 A1 | 12/2009 | LaVon et al. | |
| 2010/0004616 A1 | 1/2010 | Nakamura et al. | |
| 2012/0061015 A1 | 3/2012 | LaVon et al. | |
| 2012/0061016 A1 | 3/2012 | LaVon et al. | |
| 2012/0222576 A1 | 9/2012 | McNeil et al. | |
| 2013/0072887 A1 | 3/2013 | LaVon et al. | |
| 2013/0211356 A1 | 8/2013 | Nishikawa et al. | |
| 2013/0255861 A1 | 10/2013 | Schneider | |
| 2013/0255862 A1 | 10/2013 | Schneider et al. | |
| 2013/0255863 A1 | 10/2013 | LaVon et al. | |
| 2013/0255864 A1 | 10/2013 | Schneider et al. | |
| 2013/0255865 A1 | 10/2013 | Brown et al. | |
| 2013/0306226 A1 | 11/2013 | Zink et al. | |
| 2017/0145636 A1 * | 5/2017 | Zhou | D21H 17/36 |

* cited by examiner

SYSTEMS AND METHODS FOR INSPECTING AND EVALUATING QUALITIES OF PRINTED REGIONS ON SUBSTRATES FOR ABSORBENT ARTICLES

FIELD OF THE INVENTION

The present disclosure relates to systems and methods for manufacturing absorbent articles, and more particularly, systems and methods for inspecting and evaluating qualities of printed regions on substrates utilized in absorbent articles.

BACKGROUND OF THE INVENTION

Along an assembly line, diapers and various types of other disposable absorbent articles may be assembled by adding components to and otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics.

For quality control purposes, absorbent article converting lines may utilize various types of sensor technology to detect various types of defects in the webs and discrete components added to the webs along the converting line as absorbent articles are constructed. Example sensor technology may include vision systems, photoelectric sensors, proximity sensors, laser or sonic distance detectors, and the like. Sensor data may be communicated to an analyzer in various ways. In turn, the analyzer may be programmed to receive sensor data and reject or cull defective diapers after the final knife cut at the end of the converting line.

In some assembly operations, graphics are printed on individual components and/or continuous webs of material used to assemble the absorbent articles. The graphics may be provided by printing ink on substrate materials by various printing methods, such as flexographic printing, rotogravure printing, screen-printing, inkjet printing, and the like. In some configurations, the printing operations are performed separate to the assembly process, such as for example, printing the substrates offline wherein the printed substrates may be stored until needed for production. For example, printing operations may be accomplished on discrete printing lines, separately from converting lines that are dedicated to manufacturing disposable absorbent articles. After printing on the printing lines, the printed substrates are delivered to the converting lines, such as in a form of continuous webs comprising printed images thereon. In some configurations, the graphic printing may be done online during the article assembly process.

However, utilizing printed substrates in converting operations may create additional challenges when attempting to maintain aesthetically pleasing final assemblies. For example, various printing operations, alone or in combination with other article assembly operations, may result in graphics having various inconsistencies with respect to the desired quality of such graphics. It is to be appreciated that various factors may determine a level of the print quality.

In some print quality inspection regiments, the print quality of printed graphics may be judged solely by human beings. In turn, such an inspection regiment is completely subjective and may result in graphics having widely variable levels of quality being included in final article assemblies. In addition, it can be very cumbersome for human beings to inspect every printed graphic, and as such, inspection regiments may rely on random spot checks to inspect relatively low quantities of printed graphics utilized in final article assemblies. As technology has advanced and in order to help mitigate the negative impacts of human subjectivity involved with evaluating print quality, some inspection systems may utilize various automated inspection devices, such as for example, cameras, densitometers, and spectrophotometers. However, it is to be appreciated that not all defects may have equal impact on consumer acceptance with respect to the print quality of graphics included in various articles. For example, a print defect located on a front side of a diaper may have a relatively large impact on consumer acceptance when compared with the same print defect located in crotch region of the diaper. In another example, a print defect located on a front side of a container, such as a bag or box, may have a relatively large impact on consumer acceptance when compared with the same print defect located on a bottom side of the container. Therefore, although inspection systems may utilize automated inspection devices, human beings are still relied upon to conduct comparisons of printed samples to target samples as part of the overall print quality evaluation.

Consequently, there remains a need to configure print quality inspection systems that no longer rely on human subjectivity, but rather, perform objective evaluations of print quality and wherein such systems be configured to evaluate all or substantially all printed graphics on substrates intended for use in final article assemblies.

SUMMARY OF THE INVENTION

In one form, a method for assessing print quality comprises steps of: generating an array of scores by soliciting and recording human feedback based on human perceptions of sample printed regions, wherein each score is correlated with at least one inspection parameter defined by a comparison of a sample image of a printed region and a target image, wherein the at least one inspection parameter is selected from the group consisting of: grayscale, color, shape, mismatch size, and mismatch location; providing a communication network; connecting a camera with the communication network; connecting an analyzer with the communication network; advancing a substrate in a machine direction, depositing ink to the substrate to create a printed region; inspecting the printed region with the camera; communicating an image of the printed region from the camera to the analyzer; comparing the image with the target image to calculate a visual quality score based on the array for the inspected printed region; and executing a control action based on the visual quality score.

In another form, a method for assessing print quality comprises steps of: generating an array of scores by soliciting and recording human feedback based on human perceptions of sample printed regions, wherein each score is correlated with at least one inspection parameter defined by a comparison of a sample image of a printed region and a target image, wherein the at least one inspection parameter is selected from the group consisting of: grayscale, color, shape, mismatch size, and mismatch location; providing a communication network; connecting a camera and a spectrophotometer with the communication network; connecting an analyzer with the communication network; advancing a substrate in a machine direction, the substrate comprising a printed region; inspecting the printed region with the camera; communicating an image of the printed region from the camera to the analyzer; comparing the image with the target image to calculate a first score based on the array for the inspected printed region; and inspecting the printed region with the spectrophotometer to measure at least one of a delta E and a dot area; calculating second score based on at least one of the measured delta E and dot area; calculating a full print quality score based on the first score and the second score; converting the substrate into discrete articles, wherein at least one discrete article comprises the printed region; and executing a control action based on the full print quality score.

In yet another form, a method for assessing print quality comprises steps of: generating an array of scores by soliciting and recording consumer feedback based on consumer perceptions of sample printed regions, wherein each score is correlated with at least one inspection parameter defined by a comparison of a sample image of a printed region and a target image, wherein the at least one inspection parameter is selected from the group consisting of: grayscale, color, shape, mismatch size, and mismatch location; providing a communication network; connecting a first camera, a second camera, and a spectrophotometer with the communication network; connecting an analyzer with the communication network; advancing a substrate in a machine direction, the substrate comprising a printed region; inspecting the printed region with the first camera; communicating an image of the printed region from the camera to the analyzer; comparing the image with the target image to calculate a first score based on the array for the inspected printed region; and inspecting the printed region with the spectrophotometer to measure a delta E and a dot area; calculating a second score based on the measured delta E; calculating a third score based on the measured dot area; inspecting the printed region with the second camera to measure a color to color registration; calculating a fourth score based on the measured color to color registration; calculating a full print quality score based on the first score, the second score, the third score, and the fourth score; converting the substrate into discrete articles, wherein at least one discrete article comprises the printed region; and executing a control action based on the full print quality score.

DETAILED DESCRIPTION OF THE INVENTION

Figure 1A:
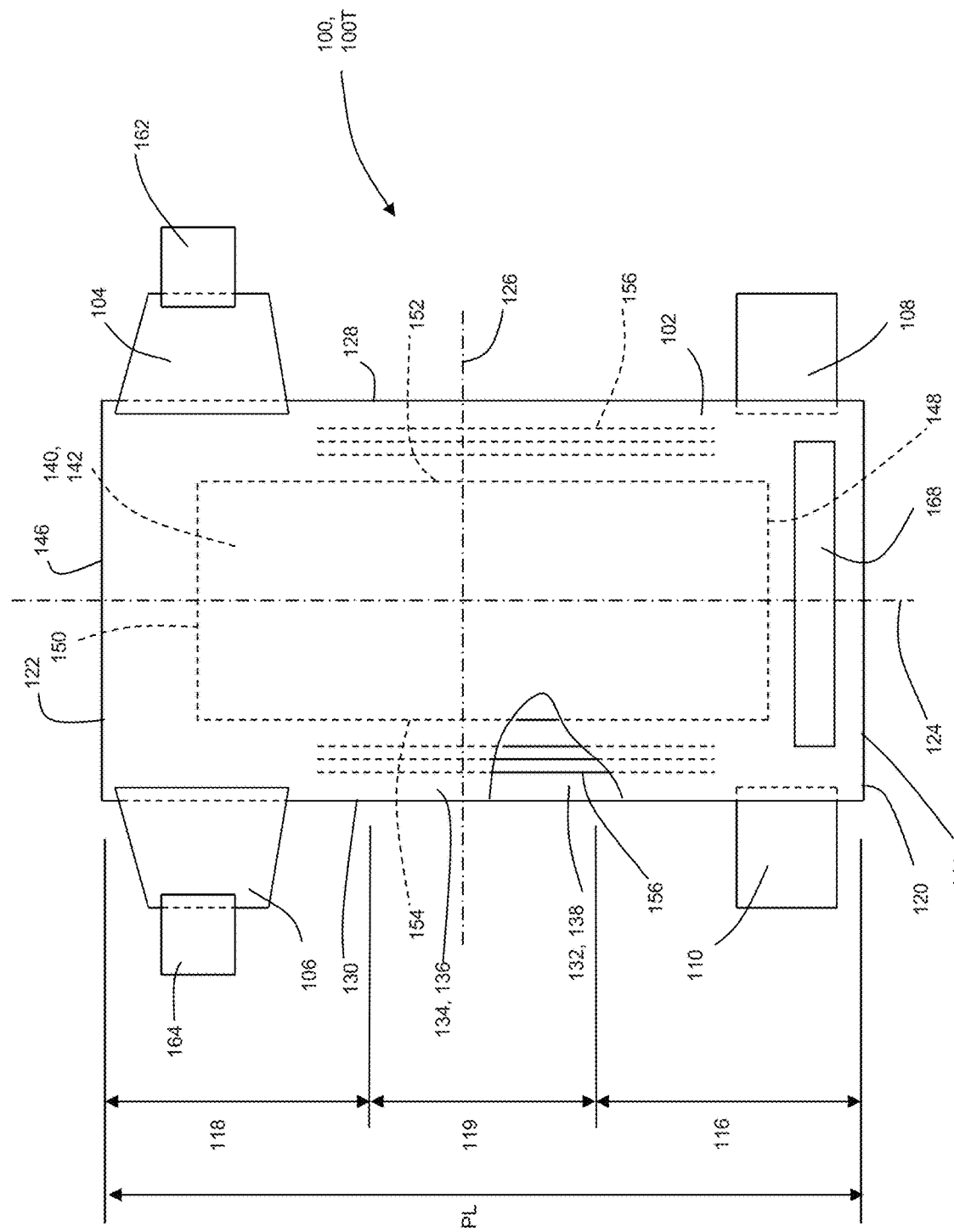
FIG. 1A is a partially cut away plan view of an absorbent article in the form of a taped diaper that may include one or more substrates with printed regions evaluated in accordance with the present disclosure with the portion of the diaper that faces away from a wearer oriented towards the viewer.

"Absorbent article" is used herein to refer to consumer products whose primary function is to absorb and retain liquids, soils, and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, paper, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674, 216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897,545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

The term "feminine hygiene articles" refers to disposable absorbent articles used by women for catamenial protection. Such feminine hygiene articles may include sanitary napkins, tampons, interlabial products, incontinence devices, and pantiliners. Non-limiting examples of panty liners and sanitary napkins include those disclosed in U.S. Pat. Nos. 4,324,246; 4,463,045; 4,342,314; 4,556,146; 4,589,876; 4,687,478; 4,950,264; 5,009,653; 5,267,992; and 6,004,893.

The present disclosure relates to systems and processes for inspecting and evaluating qualities of printed regions on substrates. As discussed in more detail below, the systems herein may include one or more communication networks connecting one or more sensors with an analyzer. The sensors may be configured in various ways, such as for example, cameras and spectrophotometers. In operation, ink is applied to a substrate to create at least one printed region, and the sensors are configured to inspect the printed region. The sensors may be configured to communicate measurements and/or images to the analyzer. And the analyzer may then calculate one or more quality subscores based on respective measurements and/or images. In turn, a full print quality score may be calculated based on one or more of the quality subscores.

As discussed in more detail below, a first quality subscore may be calculated based on an array of scores generated by soliciting and recording consumer feedback based on consumer perceptions of sample printed regions. Each score is correlated with at least one inspection parameter defined by a comparison of a sample image of a printed region and a target image. The at least one inspection parameter may be selected from the group consisting of: grayscale, color, shape, mismatch size, and mismatch location. In operation, a first camera inspects the printed region and communicates an image of the printed region to the analyzer. The analyzer compares the image with the target image to calculate a first quality subscore based on the array for the inspected printed region. In addition, the printed region may be inspected with the spectrophotometer to measure a delta E and a dot area. As such, the analyzer may calculate a second quality subscore based on the measured delta E and a third quality subscore based on the measured dot area. The printed region may also be inspected with a second camera to measure a color to color registration, and as such, a fourth quality subscore may be calculated based on the measured color to color registration. In turn, a full print quality score may be calculated based on one or more of the first score, the second score, the third score, and the fourth score. The analyzer may then execute a control action based on the full print quality score. Thus, the systems and methods herein may be configured to eliminate human involvement in performing visual checks when evaluating print quality, and may also be configured to check all or substantially all printed materials, as opposed to relying on random spot checks.

It is to be appreciated that the inspected products may include regions and print aspects having varying levels of importance. Thus, the analyzer may utilize an algorithm that may be configured to weigh all measured data according to the respective importance of such data in relation to the overall product appearance. In addition, the algorithm may be adapted individually to the print images on different products. Further, the inspection process may be applied to varying quantities of products, for example, from one product to pluralities of products, wherein unique inspections of a single product can be tracked as such.

Figure 1B:
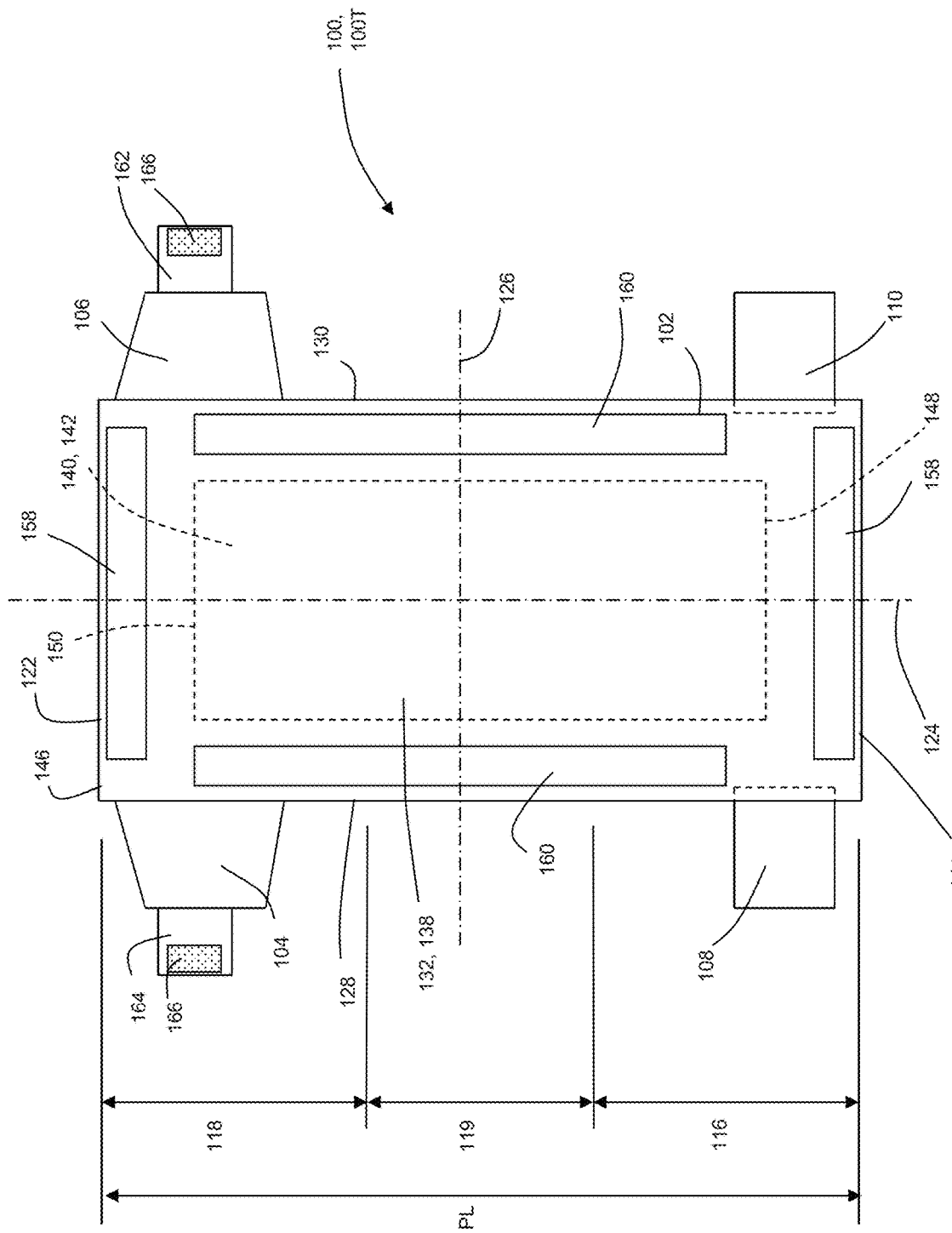
FIG. 1B is a plan view of the absorbent article of FIG. 1A that may include one or more substrates with printed regions evaluated in accordance with the present disclosure with the portion of the diaper that faces toward a wearer oriented towards the viewer.

It is to be appreciated that the systems and methods disclosed herein are applicable to work with various types of converting processes and/or machines, such as for example, absorbent article manufacturing, packaging, and/or printing processes. In some configurations, the methods and apparatuses may be utilized in the manufacture of diapers. And for the purposes of a specific illustration, FIGS. 1A and 1B show an example of an absorbent article 100 that may be assembled in accordance with the methods and apparatuses disclosed herein. In particular, FIG. 1A shows one example of a plan view of an absorbent article 100 configured as a taped diaper 100T, with the portion of the diaper that faces away from a wearer oriented towards the viewer. And FIG. 1B shows a plan view of the diaper 100 with the portion of the diaper that faces toward a wearer oriented towards the viewer. The taped diaper 100T shown in FIGS. 1A and 1B includes a chassis 102, first and second rear side panels 104 and 106; and first and second front side panels 108 and 110.

As shown in FIGS. 1A and 1B, the diaper 100 and the chassis 102 each include a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The absorbent article may also include a laterally extending front waist edge 120 in the front waist region 116 and a longitudinally opposing and laterally extending back waist edge 122 in the back waist region 118. To provide a frame of reference for the present discussion, the diaper 100T in FIGS. 1A and 1B is shown with a longitudinal axis 124 and a lateral axis 126. The longitudinal axis 124 may extend through a midpoint of the front waist edge 120 and through a midpoint of the back waist edge 122. And the lateral axis 126 may extend through a midpoint of a first longitudinal or right side edge 128 and through a midpoint of a second longitudinal or left side edge 130.

As shown in FIGS. 1A and 1B, the diaper 100 includes an inner, body facing surface 132, and an outer, garment facing surface 134. And the chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs, an elastic waist region, and/or flaps, e.g., side panels and/or ears, to enhance the fits around the legs and waist of the wearer, to enhance the fit around the legs of the wearer.

As shown in FIGS. 1A and 1B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 1A, the laterally extending end edges 144 and 146 may form a portion of the laterally extending front waist edge 120 in the front waist region 116 and a portion of the longitudinally opposing and laterally extending back waist edge 122 in the back waist region 118. The distance between the first lateral end edge 144 and the second lateral end edge 146 may define a pitch length, PL, of the chassis 102. When the diaper 100 is worn on the lower torso of a wearer, the front waist edge 120 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio (acquired by Berry Global), under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper 100 may also include an absorbent assembly 140 that is joined to the chassis 102. As shown in FIGS. 1A and 1B, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1.

As previously mentioned, the diaper 100 may also include elasticized leg cuffs 156 and an elasticized waistband 158. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; and U.S. Patent Publication No. 2009/0312730 A1.

The elasticized waistband 158 may provide improved fit and containment and may be a portion or zone of the diaper 100 that may elastically expand and contract to dynamically fit a wearer's waist. The elasticized waistband 158 may extend longitudinally inwardly from the waist edges 120, 122 of the diaper toward the lateral edges 148, 150 of the absorbent core 142. The diaper 100 may also include more than one elasticized waistband 158, for example, having one waistband 158 positioned in the back waist region 118 and one waistband 158 positioned in the front wait region 116, although other embodiments may be constructed with a single elasticized waistband 158. The elasticized waistband 158 may be constructed in a number of different configurations including those described in U.S. Pat. Nos. 4,515,595 and 5,151,092. In some embodiments, the elasticized waistbands 158 may include materials that have been "prestrained" or "mechanically prestrained" (subjected to some degree of localized pattern mechanical stretching to permanently elongate the material). The materials may be prestrained using deep embossing techniques as are known in the art. In some embodiments, the materials may be prestrained by directing the material through an incremental mechanical stretching system as described in U.S. Pat. No. 5,330,458. The materials are then allowed to return to their substantially untensioned condition, thus forming a zero strain stretch material that is extensible, at least up to the point of initial stretching. Examples of zero strain materials are disclosed in U.S. Pat. Nos. 2,075,189; 3,025,199; 4,107,364; 4,209,563; 4,834,741; and 5,151,092.

As shown in FIG. 1B, the chassis 102 may include longitudinally extending and laterally opposing side flaps 160 that are disposed on the interior surface 132 of the chassis 102 that faces inwardly toward the wearer and contacts the wearer. Each side flap may have a proximal edge. The side flaps may also overlap the absorbent assembly 140, wherein the proximal edges extend laterally inward of the respective side edges of the absorbent assembly 152 and 154. In some configurations, the side flaps may not overlap the absorbent assembly. It is to be appreciated that the side flaps may be formed in various ways, such as for example, by folding portions of the chassis 102 laterally inward, i.e., toward the longitudinal axis 124, to form both the respective side flaps and the side edges 128 and 130 of the chassis 102. In another example, the side flaps may be formed by attaching an additional layer or layers to the chassis at or adjacent to each of the respective side edges and of the chassis. Each of the side flaps may be joined to the interior surface 132 of the chassis and/or the absorbent assembly in side flap attachment zones in the front waist region 116 and in side flap attachment zones in the back waist region 118. The side flaps may extend to the same longitudinal extent as the absorbent article or alternatively the side flaps may have a longitudinal extent that is less than the absorbent article.

Taped diapers may be manufactured and provided to consumers in a configuration wherein the front waist region and the back waist region are not fastened, pre-fastened, or connected to each other as packaged, prior to being applied to the wearer. For example, the taped diaper 100 may be folded about a lateral centerline with the interior surface 132 of the first waist region 116 in surface to surface contact with the interior surface 132 of the second waist region 118 without fastening or joining the waist regions together. The rear side panels 104 and 106 and/or the front side panels 108 and 110 may also be folded laterally inward toward the inner surfaces 132 of the waist regions 116 and 118.

The diaper 100 may also include various configurations of fastening elements to enable fastening of the front waist region 116 and the back waist region 118 together to form a closed waist circumference and leg openings once the diaper is positioned on a wearer. For example, as shown in FIGS. 1A and 1B, the diaper 100 may include first and second fastening members 162, 164, also referred to as tabs, connected with the first and second rear side panels 104, 106, respectively. The diaper may also include first and second front side panels 108, 110, that may or may not include fastening members.

With continued reference to FIGS. 1A and 1B, each side panel 104, 106 and/or fastening member 162 and 164 may form a portion of or may be permanently bonded, adhered or otherwise joined directly or indirectly to the chassis 102 laterally inward from the side edge 128 and 130, in one of the front waist region 116 or the back waist region 118. Alternatively, the fastening members 162, 164 may form a portion of or may be permanently bonded, adhered or otherwise joined directly or indirectly to the first and second rear panels 104, 106 at or adjacent the distal edge of the panel and/or the first and second front side panels 108 and 110 at or adjacent the distal edge of the side panel. It is to be appreciated that the fastening members and/or side panels may be assembled in various ways, such as disclosed for example, in U.S. Pat. No. 7,371,302. The fastening members 162, 164 and/or side panels 104, 106, 108, 110 may also be permanently bonded or joined at or adjacent the side edges 128 and 130 of the chassis 102 in various ways, such as for example, by adhesive bonds, sonic bonds, pressure bonds, thermal bonds or combinations thereof, such as disclosed for example, U.S. Pat. No. 5,702,551.

Referring now to FIG. 1B, the first fastening member 162 and/or the second fastening member 164 may include various types of releasably engageable fasteners. The first and second fastening members 162 and/or 164 may also include various types of refastenable fastening structures. For example, the first and second fastening members 162 and 164 may include mechanical fasteners, 166, in the form of hook and loop fasteners, hook and hook fasteners, macrofasteners, buttons, snaps, tab and slot fasteners, tape fasteners, adhesive fasteners, cohesive fasteners, magnetic fasteners, hermaphroditic fasteners, and the like. Some examples of fastening systems and/or fastening members 162, 164 are discussed in U.S. Pat. Nos. 3,848,594; 4,662,875; 4,846,815; 4,894,060; 4,946,527; 5,151,092; 5,221,274; 6,251,097; 6,669,618; 6,432,098; and U.S. Patent Publication Nos. 2007/0078427 A1 and 2007/0093769 A1.

Figure 1C:
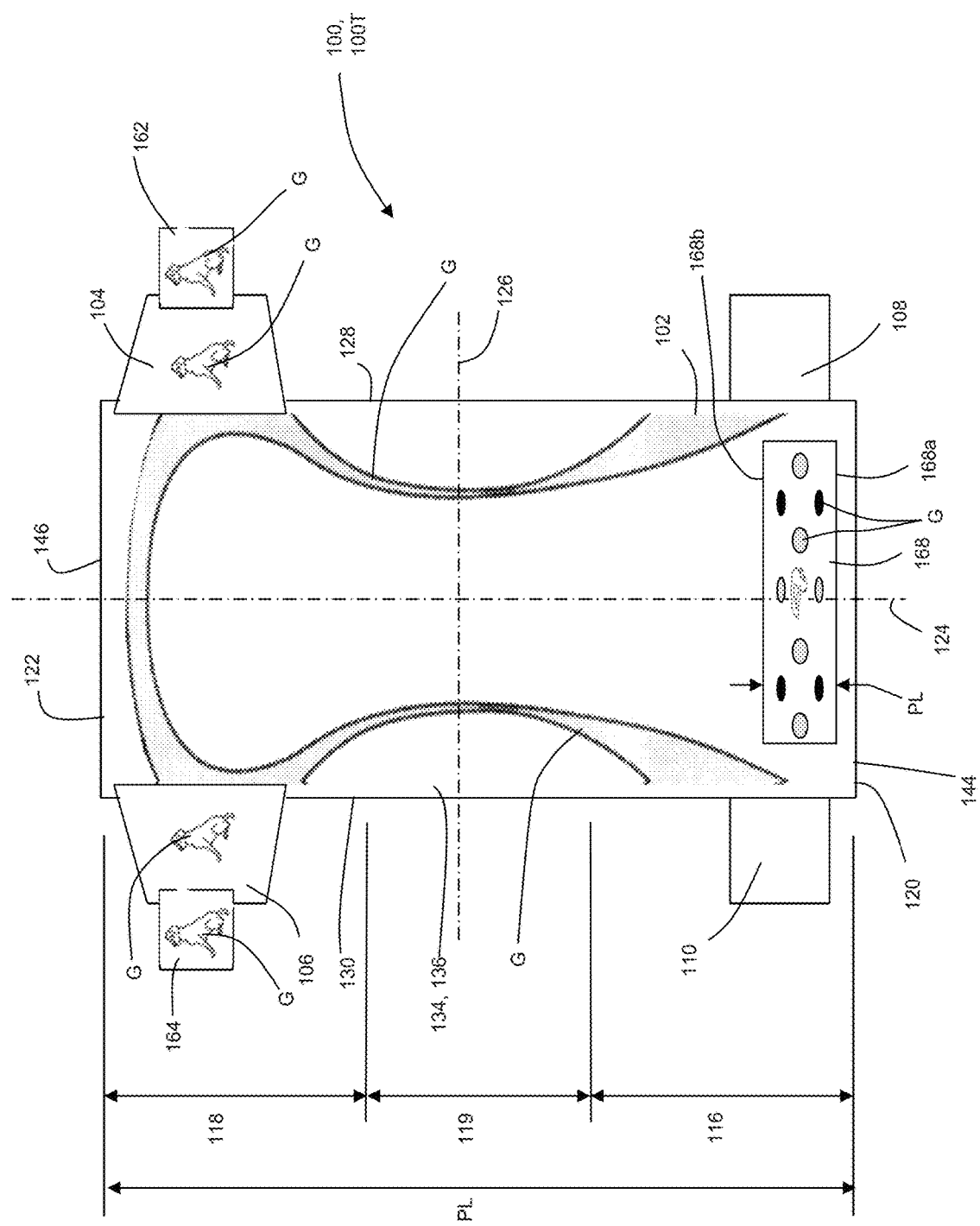
FIG. 1C is a plan view of a diaper with graphics on a backsheet, side panels, and a connection zone.

As previously mentioned, the fastening members 162 and 164 may be constructed from various materials and may be constructed as a laminate structure. The fastening members 162 and 164 may also be adapted to releasably and/or refastenably engage or connect with another portion of the diaper 100. For example, as shown in FIG. 1A, the diaper 100 may include a connection zone 168, sometimes referred to as a landing zone, in the first waist region 116. As such, when the taped diaper 100 is placed on a wearer, the fastening members 162 and 164 may be pulled around the waist of the wearer and connected with the connection zone 168 in the first waist region 116 to form a closed waist circumference and a pair of laterally opposing leg openings. It is to be appreciated that the connection zone may be constructed from a separate substrate that is connected with the chassis 102 of the taped diaper, such as shown in FIG. 1C. As such, the connection zone 168 may have a pitch length PL defined by a distance extending between a first lateral end edge 168a and the second lateral end edge 168b. In some embodiments, the connection zone may be integrally formed as part of the backsheet 136 of the diaper 100 or may be formed as part of the first and second front panels 108, 110, such as described in U.S. Pat. Nos. 5,735,840 and 5,928,212.

Figure 2A:
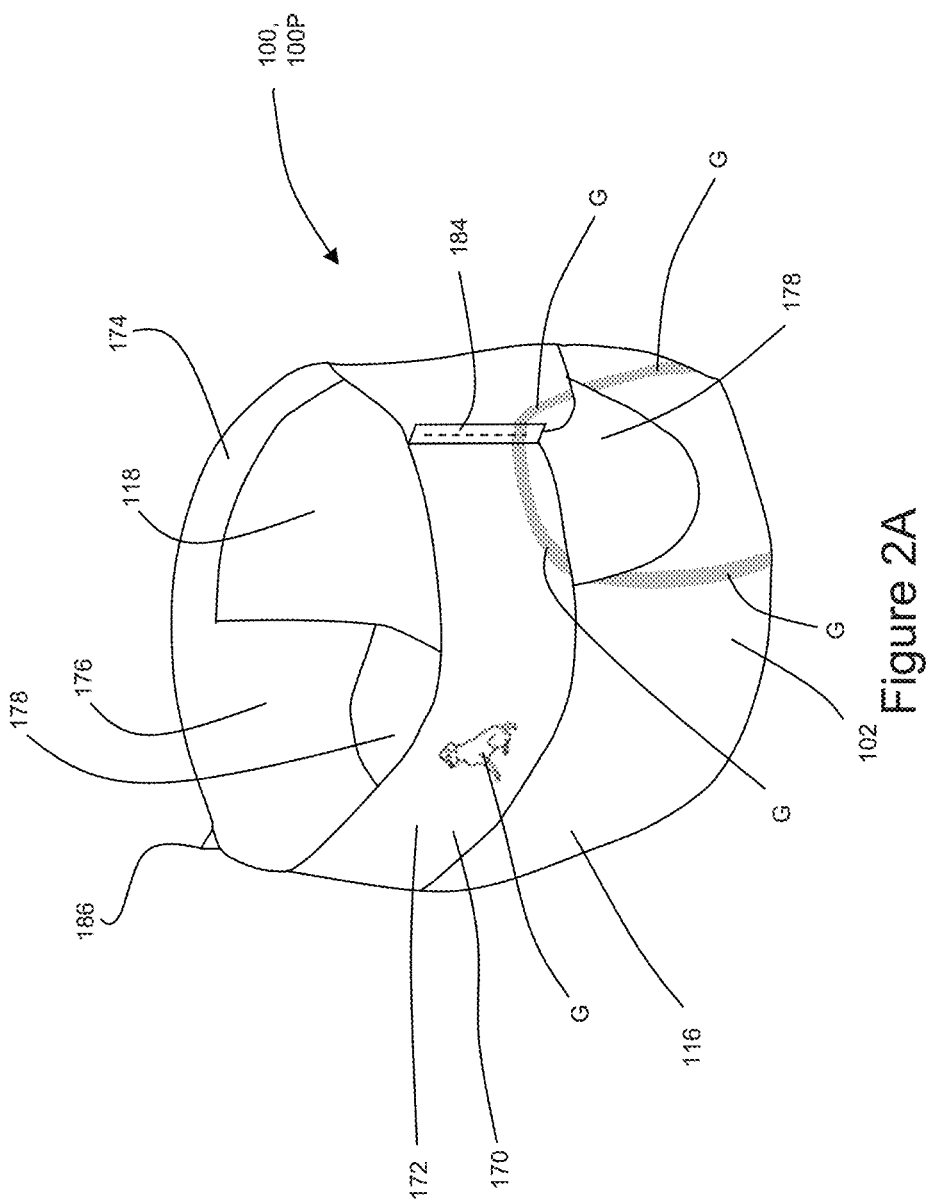
FIG. 2A is a front perspective view of an absorbent article in the form of a diaper pant with printed regions on a chassis and front and rear belts.
Figure 2B:
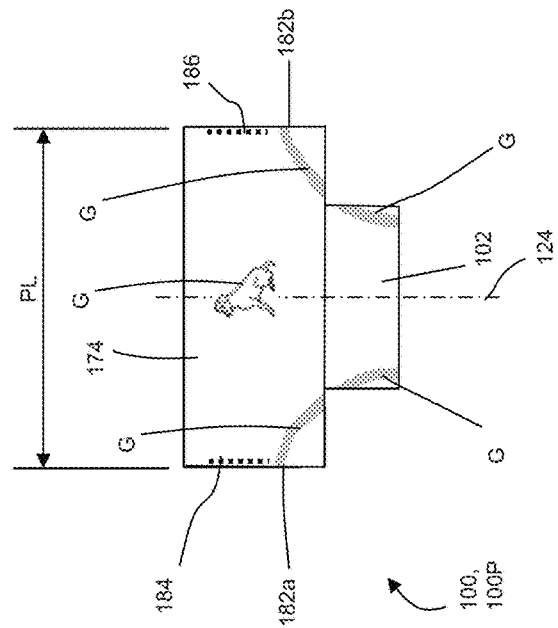
FIG. 2B is a front view of the absorbent article of FIG. 2A.
Figure 2C:
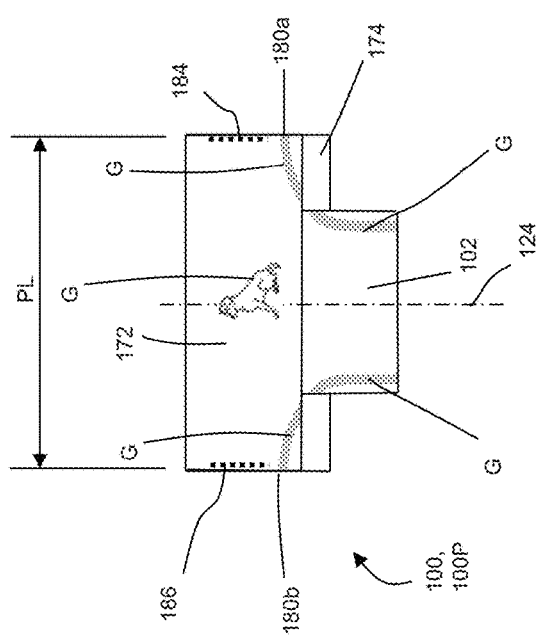
FIG. 2C is a rear view of the absorbent article of FIG. 2A.

As previously mentioned, absorbent articles 100 may also be configured as diaper pants 100P having a continuous perimeter waist opening and continuous perimeter leg openings. For example, FIG. 2A shows a perspective view of an absorbent article 100 in the form of a diaper pant 100P in a pre-fastened configuration, and FIGS. 2B-2C show front and rear plan views of the diaper pant 100P. The diaper pant 100P may include a chassis 102 such a discussed above with reference to FIG. 1A and a ring-like elastic belt 170 such as shown in FIG. 2A. In some embodiments, a first elastic belt 172 and a second elastic belt 174 are bonded together to form the ring-like elastic belt 170. As such, diaper pants may be manufactured with the ring-like elastic belt 174 and provided to consumers in a configuration wherein the front waist region 116 and the back waist region 118 of the chassis 102 are connected to each other as packaged, prior to being applied to the wearer. As such, diaper pants may have a continuous perimeter waist opening 176 and continuous perimeter leg openings 178 such as shown in FIG. 2A.

As previously mentioned, the ring-like elastic belt 170 may be defined by a first elastic belt 172 connected with a second elastic belt 174. As shown in FIGS. 2A-2C, the first elastic belt 172 extends between a first longitudinal side edge 180a and a second longitudinal side edge 180b. And the second elastic 174 belt extends between a first longitudinal side edge 182a and a second longitudinal side edge 182b. The distance between the first longitudinal side edge 180a and the second longitudinal side edge 180b defines a pitch length, PL, of the first elastic belt 172, and the distance between the first longitudinal side edge 182a and the second longitudinal side edge 182b defines the pitch length, PL, of the second elastic belt 174. The first elastic belt is connected with the first waist region 116 of the chassis 102, and the second elastic belt 108 is connected with the second waist region 116 of the chassis 102. As shown in FIGS. 2A-2C, opposing end regions of the first elastic belt 172 are connected with opposing end regions of the second elastic belt 174 at a first side seam 184 and a second side seam 186 to define the ring-like elastic belt 170 as well as the waist opening 176 and leg openings 178. It is to be appreciated that the ring-like elastic belt may be formed by joining a first elastic belt to a second elastic belt with permanent side seams or with openable and reclosable fastening systems disposed at or adjacent the laterally opposing sides of the belts.

As previously mentioned, absorbent articles may be assembled with various components that may be printed off-line, before assembly, or on-line, as part of the assembly process. As such, the absorbent articles herein may include graphics printed on various components. Thus, in the context of the previous discussion, the apparatuses and methods herein may be used to inspect and evaluate printed regions of substrates configured as continuous substrates and/or discrete components of an absorbent article 100, either off-line or on-line. As such, the systems and methods herein may be utilized to inspect and evaluate such graphics before, during, and/or after assembly. In some examples, graphic inspection may be carried out on a substrate immediately or shortly after printing. In some examples, graphic inspections may be carried out on a substrate as before and/or during advancement to an assembly process. In some examples, the graphic inspections may be carried out on a substrate that is part of an assembled product.

Figure 3:
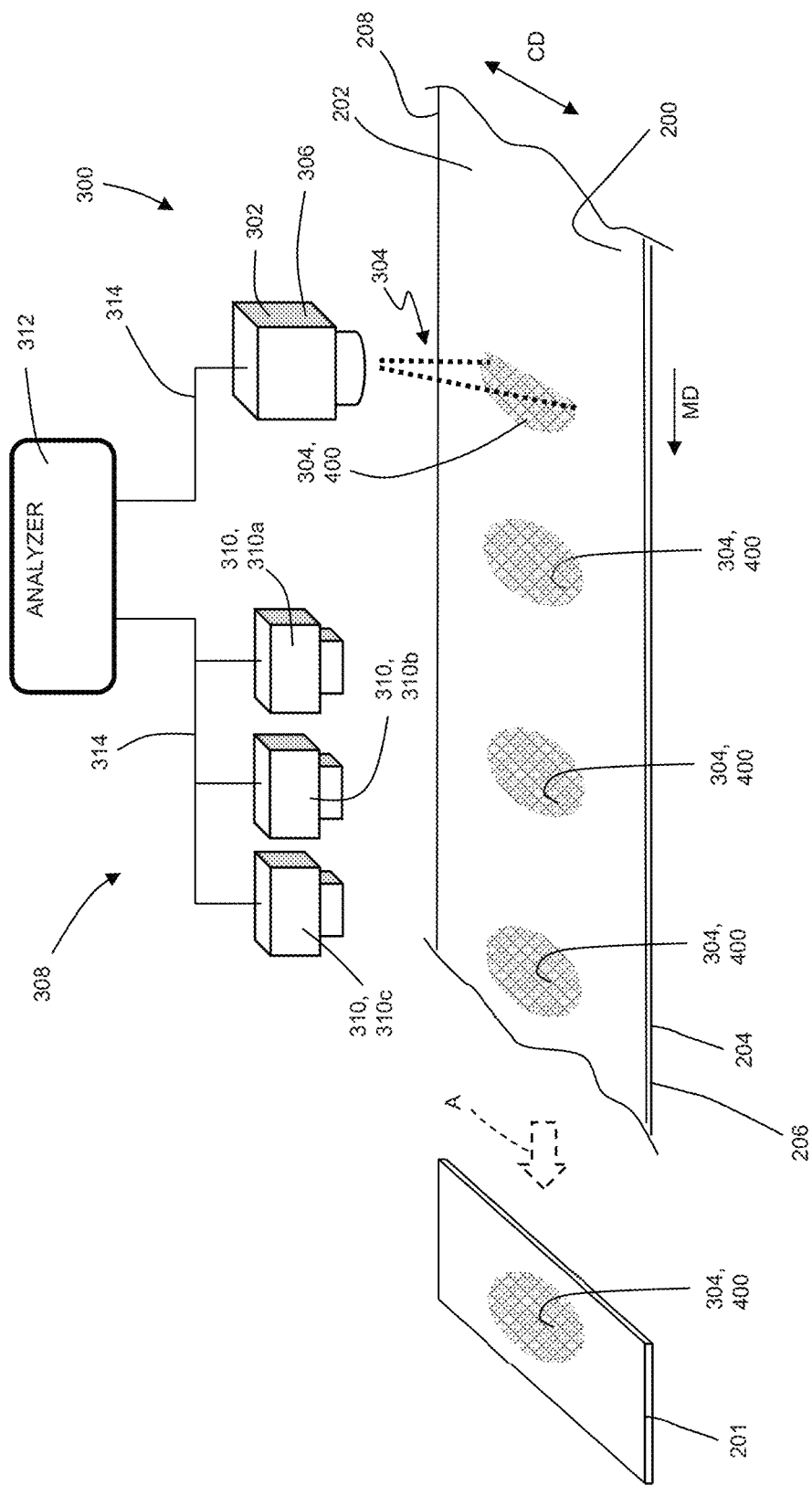
FIG. 3 is a schematic isometric view of a system for inspecting and evaluating the quality of printed regions on a substrate.

FIG. 3 shows a schematic representation of a converting process including a printing apparatus or system 300 for printing graphics on a substrate 200 advancing in a machine direction MD. The substrate 200 may be a continuous substrate and may include a first surface 202 and an opposing second surface 204. The substrate 200 may also define a width extending in the cross direction CD between a first longitudinal side edge 206 and a second longitudinal side edge 208. The printing system 300 may include a single or multi-step printing station 302. During operation, the substrate 200 advances in the machine direction MD. In turn, the printing station 302 deposits ink 304 onto the first surface 202 of the advancing substrate 200 to define a printed region 400. It is to be appreciated that the substrate 200 may be subjected to additional manufacturing and converting operations, such as combining and/or cutting operations, during assembly of an article. Such additional manufacturing operations are represented by the dashed arrow A that generically represents converting the substrate into at least one discrete article 201 that includes the printed region 400.

It is to be appreciated that the printed substrate 200 may be utilized as a component of various types of discrete articles 201 that may be in various forms and types. For example, the discrete articles 201 herein may configured as absorbent articles, feminine hygiene articles, diapers, sanitary napkins, panty liners, printed labels, and containers such as bottles, bags, and boxes. Thus, it is to be appreciated that the printed substrates 200 herein may be in the form of various types of materials used to construct such discrete articles 201.

Various examples of materials are provided with respect to the absorbent article discussed above with reference to FIGS. 1A-1C and 2A-2C. As such, the apparatuses and methods herein may be configured to inspect and evaluate the quality printed regions on substrates applied to any of the topsheet 138; backsheet 136; absorbent core 140; leg cuffs 156; waist feature 158; side panels 104, 106, 108, 110; connection zones 168; fastening elements 162, 164, 166, and/or belts before, during, and/or after the manufacture of an absorbent article 100. For example, the backsheet 136 of the taped diaper 100T shown in FIG. 1C includes graphics G that may be inspected and evaluated before, during, and/or after assembly. The connection zone 168 and the side panels 104, 106, and fastening members 162, 164 shown in FIG. 1C may also include graphics G inspected and evaluated before, during, and/or after assembly. In yet another example, the front belt 172 and rear belt 174 of the diaper pant 100P may include graphics G inspected and evaluated before, during, and/or after assembly. In additional examples, containers and/or labels may be configured in various shapes and sizes and may be formed from various types of material, such as cardboard material and/or film materials. Such film materials may be made of paper, plastic, and/or various types of recyclable material, and may also comprise a laminate structure of two or more materials. Film materials may also comprise polymeric films, polypropylene films, and/or polyethylene films.

The printed region 400 is generically represented herein as an oval shape on the first surface 202 of the substrate 200. It is to be appreciated that the printing station 302 can be configured to print a plurality of printed regions arranged along the machine direction MD and/or cross direction of the substrate 200. It is also to be appreciated that a single printed region 400 or a plurality of printed regions 400 may form a graphic. As used herein, the term "graphic" refers to images or designs that are constituted by a figure (e.g., a line(s)), a symbol or character, a color difference or transition of at least two colors, or the like. A graphic may include an aesthetic image or design that can provide certain benefit (s) when viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink or spot colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic. It is also to be appreciated that colors of inks may be outside the area of human-visible spectrum, for example, such as inks that can be detected with specific wave lengths, such as ultraviolet (UV) reactive inks.

It is to be appreciated that the printing station 302 may be configured in various ways and may include various types of printing accessories. For example, the printing station 302 may include a printer 306, which may be configured in various ways. In some configurations, the printing station 302 may also include a corona treater, which may be positioned upstream of the printer 306. The corona treater may be configured to increase the surface energy of the surface of the substrate 200. For example, the corona treater may be configured to increase the surface energy of the surface to be printed to about 42 dynes/cm. In some configurations, the printer 306 may be in the form of a flexographic printer. In particular, a flexographic printer may utilize printing plates made of rubber or plastic with a slightly raised image thereon. The inked plates are rotated on a cylinder which transfers the image to the sheet. Some configurations may include a printer 306 in the form of a gravure printer. Gravure printing may utilize an image etched on the surface of a metal plate. The etched area is filled with ink and the plate is rotated on a cylinder that transfers the image to the substrate. In some configurations, printing devices such as disclosed in U.S. Patent Publication No. 2012/0222576 A1 may be used. In some configurations, the printer 306 may include various quantities of non-contact printheads arranged and/or configured in various ways to deposit inks onto the advancing substrate 200 to create printed regions 400. For example, in some embodiments, the printheads herein may be configured as inkjet printheads. Inkjet printing is a non-impact dot-matrix printing technology in which droplets of ink are jetted from a small orifice in the printhead directly to a specified position on a substrate to create a graphic. The inkjet printheads herein may be configured to perform different types of inkjet printing, such as for example, "drop-on-demand" and "continuous" inkjet printing.

With "continuous" inkjet printing processes, an ink is supplied under pressure to an inkjet nozzle and forced out through a small orifice. Prior to passing out of the nozzle, the pressurized ink stream proceeds through a ceramic crystal, which is subjected to an electric current. The electric current causes a piezoelectric vibration equal to the frequency of an AC electric current. The vibration, in turn, generates the ink droplets from the unbroken ink stream. As such, the ink stream breaks up into a continuous series of drops which are equally spaced and of equal size. Surrounding the jet, at a point where the drops separate from the fluid stream in a charge electrode, a voltage is applied between the charge electrode and the drop stream. When the drops break off from the stream, each drop carries a charge proportional to the applied voltage at the instant at which it breaks off. By varying the charge electrode voltages at the same rate as drops are produced, it is possible to charge every drop to a predetermined level. The drop stream passes between two deflector plates which are maintained at a constant potential that deflects a drop towards one of the plates by an amount proportional to the charge carried. Drops that are uncharged are undeflected and collected into a gutter to be recycled to the ink nozzle. Those drops which are charged, and hence deflected, impinge on a substrate traveling at a high speed at right angles to the direction of drop deflection. By varying the charge on individual drops, a desired pattern can be printed.

With "drop-on-demand" inkjet printing processes, an ink is forced under pressure from the printhead through a relatively small orifice in the form of minute droplets by rapid pressure impulses. In some configurations, the orifice may have a diameter of about 0.0024 inches (5-50 microns). The rapid pressure impulses may be generated in the printhead by either expansion of a piezoelectric crystal vibrating at a high frequency or volatilization of a volatile composition (e.g. solvent, water, propellant) within the ink by rapid heating cycles. The piezoelectric crystal expansion causes the ink to pass through the orifice as minute droplets in proportion to the number of crystal vibrations. Thermal inkjet printers employ a heating element within the print head to volatilize a portion of the composition that propels the vast majority of fluid through the orifice nozzle to form droplets in proportion to the number of on-off cycles for the heating element. The ink is forced out of the nozzle when needed to print a spot on a substrate as part of a desired image. The minute droplets may also be energized to achieve an electrical charge and deflected as in the continuous inkjet printing process discussed above. Various inkjet printing processes are more particularly described in U.S. Pat. Nos. 3,465,350; 3,465,351; and 9,211,356.

Although the printing station 302 may include a single printhead, it is to be appreciated that printing stations 302 herein may be configured with more than one printhead arranged in the cross direction CD and/or machine direction MD. In some configurations, the printing stations 302 herein may include backup printheads, such as disclosed in U.S. Pat. No. 6,811,239. It is also to be appreciated that the printheads may be configured to print inks having the same colors or different colors. For example, a first ink may comprise a first color, and a second ink may comprise a second color different from the first color. In another example, a first ink may comprise a first color, and a second ink may comprise a second color that is the same as the first color. In addition, the printheads herein may be configured to perform single color, multi-color, halftone, and process printing.

"Halftone" or "halftoning" as used herein, sometimes referred to as "screening," is a printing technique that allows for less-than-full saturation of the primary colors. In halftoning, relatively small dots of each primary color are printed in a pattern small enough such that the average human observer perceives a single color. For example, magenta printed with a 20% halftone will appear to the average observer as the color pink. The reason for this is because, without wishing to be limited by theory, the average observer may perceive the tiny magenta dots and white paper between the dots as lighter, and less saturated, than the color of pure magenta ink. A "base color," as used herein, refers to a color that is used in the halftoning printing process as the foundation for creating additional colors. In some non-limiting embodiments, a base color is provided by a colored ink. Non-limiting examples of base colors may be selected from the group consisting of: cyan, magenta, yellow, black, red, green, and blue-violet. "Black", as used herein, refers to a color and/or base color which absorbs wavelengths in the entire spectral region of from about 380 nm to about 740 nm. "Cyan", as used herein, refers to a color and/or base color which have a local maximum reflectance in the spectral region of from about 390 nm to about 570 nm. In some embodiments, the local maximum reflectance is between the local maximum reflectance of the blue or blue-violet and green local maxima. "Magenta", as used herein, refers to a color and/or base color which have a local maximum reflectance in the spectral region of from about 390 nm to about 490 nm and 621 nm to about 740 nm. "Yellow", as used herein, refers to a color and/or base color which have a local maximum reflectance in the spectral region of from about 571 nm to about 620 nm.

"Process Printing," as used herein, refers to the method of providing color prints using at least three of the primary of colors cyan, magenta, yellow and black. Each layer of color is added over a base substrate. In some embodiments, the base substrate is white or off-white in color. With the addition of each layer of color, certain amounts of light are absorbed (those of skill in the printing arts will understand that the inks actually "subtract" from the brightness of the white background), resulting in various colors. CMY (cyan, magenta, yellow) are used in combination to provide additional colors. Non-limiting examples of such colors are red, green, and blue. K (black) is used to provide alternate shades and pigments. One of skill in the art will appreciate that CMY may alternatively be used in combination to provide a black-type color.

It is also to be appreciated that the printing system 300 herein may be configured to operate with various types of inks or ink systems, such as solvent-based, water-based, and ultraviolet (UV) cured inks. An "ink" is a liquid containing coloring matter, for imparting a particular hue to a substrate. An ink may include dyes, pigments, organic pigments, inorganic pigments, and/or combinations thereof. A non-limiting example of an ink would encompass spot colors. Additional non-limiting examples of inks include inks having white color. Additional non-limiting examples of inks include hot melt inks.

Some primary differences among the ink systems may relate to the method used for drying or curing the ink. For example, solvent-based and water-based inks are dried by evaporation, while UV cured inks are cured by chemical reactions. Inks may also include components, such as solvents, colorants, resins, additives, and (for ultraviolet inks only) UV-curing compounds, that are responsible for various functions. Some inks may be in the form of hybrid inks composed of energy curable ingredients in an aqueous solution. In some configurations, a multi-stage printing system may be utilized. In some configurations, to improve ink rub-off resistance, ink compositions used herein may contain a wax. Such waxes may include a polyethylene wax emulsion. Addition of a wax to the ink composition may enhance rub resistance by setting up a barrier which inhibits the physical disruption of the ink film after application of the ink to the fibrous sheet. Based on weight percent solids of the total ink composition, addition ranges for the wax may be from about 0.5% solids to 10% solids. An example polyethylene wax emulsion is JONWAX 26 supplied by S.C. Johnson & Sons, Inc. of Racine, Wis.

Some embodiments may utilize inks such as Artistri® Inks available from DuPont™, including 500 Series Acid Dye Ink; 5000 Series Pigment Ink; 700 Series Acid Dye Ink; 700 Series Disperse Dye Ink; 700 Series Reactive Dye Ink; 700 Series Pigment Ink; 2500 Series Acid Dye Ink; 2500 Series Disperse Dye Ink; 2500 Series Reactive Dye Ink; 2500 Series Pigment Dye Ink; 3500 Series Disperse Dye Ink; 3500 Series Pigment Dye Ink; and Solar Brite™ Ink. Ink such as disclosed in U.S. Pat. No. 8,137,721 may also be utilized. Water-based inks that may be utilized are available from Environmental Inks and Coatings Corporation, Morganton, N.C., under the following code numbers: EH034677 (yellow); EH057960 (magenta); EH028676 (cyan); EH092391 (black); EH034676 (orange); and EH064447 (green). Some embodiments may utilize water based inks composed of food-grade ingredients and formulated to be printed directly onto ingestible food or drug products, such as Candymark Series inks available in colors such as black pro, red pro, blue pro, and yellow pro, available from Inkcups located in Danvers, Mass. Other broad ranges of general purpose and specialty inks may also be used, including food grade inks available from Videojet Technologies Inc. located in Wood Dale, Ill. Additional example inks include Collins 186-150-6 LED Cyan Ink; Collins 186-150-7 LED Magenta Ink; Collins 186-150-6 LED Yellow Ink; Collins 186-150-5 LED Black Ink; and Videojet Ink 99-51SR.

With continued reference to FIG. 3, a print inspection system 308 may be configured to inspect and evaluate the print quality of the printed regions 400 on the substrate 200. In some configurations, the print inspection system 308 may include one or more sensors 310 adapted to sense various properties of the printed regions 400. The sensors 310 may be arranged adjacent the advancing substrate 200, and the sensors 310 may communicate with an analyzer 312. As discussed in more detail below, based on such communications from the sensors 310, the analyzer 312 may calculate a full print quality score and a visual quality score. In turn, the analyzer 312 may execute a control action based on the visual quality score and/or the full print quality score. It is to be appreciated that the analyzer 312 may be configured to execute various types of control actions, such as for example, rejecting a discrete article 201, providing a suggested corrective action, affecting the operation of the printer, increase or decrease advancement speeds of the substrate 200, and/or repositioning the substrate 200 in the cross direction CD. As such, the print inspection system 308 may be configured to interact with, monitor, and/or control printing operations and/or a converting line.

It is to be appreciated that the analyzer 312 may be configured in various ways. For example, the analyzer 312 may be in the form of a personal computer (PC), a central processing unit (CPU), a field programmable gate array (FPGA), an application specific integrated circuit (ASIC), or a graphical processing unit (GPU). FPGA examples may include the National Instruments PCIe-1473R, National Instruments PXIe-1435, National Instruments 1483R with FlexRIO FPGA module, Altera Stratix II, Altera Cyclone III, Xilinx Spartan 6, Xilink Vertex 6 or Vertex 7. GPU examples may include GeForce GTX 780 (Ti), Quadro K6000, Radeon R9 295X2 and Radeon HD 8990.

It is to be appreciated that the analyzer 312 may also be configured to communicate with one or more computer systems, such as for example, a programmable logic controller (PLC) and/or personal computer (PC) running software and adapted to communicate on an EthernetIP network. Some embodiments may utilize industrial programmable controllers such as the Siemens S7 series, Rockwell ControlLogix, SLC or PLC 5 series, or Mitsubishi Q series. The aforementioned embodiments may use a personal computer or server running a control algorithm such as Rockwell SoftLogix or National Instruments Labview or may be any other device capable of receiving inputs from sensors, performing calculations based on such inputs and generating control actions through servomotor controls, electrical actuators or electro-pneumatic, electrohydraulic, and other actuators. In some configurations, the systems herein may utilize a print quality management program wherein the system may upload quality data in a data center where a printer, color separator, and/or customer may view the data remotely and analyze the data for printing quality improvement. Examples of such print quality management programs are available from for example Schawk (ColorDrive), and X-rite (ColorCert). Process and product data may be stored directly in the aforementioned computer systems or may be located in a separate data historian. In some embodiments, the historian is a simple data table in the controller. In other embodiments, the historian may be a relational or simple database. Common historian applications include Rockwell Automation Factory Talk Historian, General Electric Proficy Historian, OSI PI, or any custom historian that may be configured from Oracle, SQL or any of a number of database applications. It is also to be appreciated that the analyzer 312 may be configured to communicate with various types of controllers and inspection sensors configured in various ways and with various algorithms to provide various types of data and perform various functions, for example, such as disclosed in U.S. Pat. Nos. 5,286,543; 5,359,525; 6,801,828; 6,820,022; 7,123,981; 8,145,343; 8,145,344; 8,244,393; and 9,910,429; and European Patent No. EP 1528907 B1, all of which are incorporated by reference herein.

As shown in FIG. 3, the analyzer 312 may be in communication with the sensors 310 through a communication network 314. As such, it is to be appreciated that the analyzer 312 may be physically located near the advancing substrate 200 and/or sensors 310 and/or may be located at another location and in communication with the sensors 310 via a wired and/or wireless network 314. In some embodiments, the communication network 314 is configured as a non-deterministic communication network, such as for example, Ethernet or Ethernet IP (industrial protocol) communication network.

It is to be appreciated that the print inspection system 308 may be configured to utilize various types of sensors 310. For example, the sensors 310 may be configured as cameras, spectrophotometers, and photo-optic sensors that receive either reflected or transmitted light. In some configurations, the sensor 310 may be configured as a camera adapted to inspect the printed region 400, generate an image, and transfer the image to the analyzer 312. Examples of such cameras are available from BST eltromat (SHARK LEX system), AVT (APOLLO system, JUPITER system), QuadTech, ISRA Vison, Grafikontrol Spa, Konica Minolta Inc. In some configurations, the sensor 310 may be configured as a spectrophotometer adapted to measure the color L*a*b*, density, and/or opacity of the printed region 400, and transfer the measurement data to the analyzer 312. Examples of such spectrophotometer are available from for example BST eltromat (iPQ-Spectral), AVT (SpectraLab), QuadTech (SpectralCam™), ISRA Vison, Techkon etc. Additional examples of sensors 310 may include simple vision based sensors such as for example: KEYENCE America CZ series RGB fiber optic sensors; SICK CS series sensors, and Banner Engineering QC series color sensors. The sensors may include red, green, blue (RGB) analog outputs that can characterize sensed registration features, such as colors of printed graphics, on advancing substrates by a unique sequence across a specific channel or a combination of channels. For example, some systems may utilize a color sensor, such as a red, green, blue (RGB) color sensor, that may be calibrated or "trained" to detect a specific registration mark color. A suitable such sensing system is available from Keyence of America, Schaumburg, Ill., as the Keyence PS56 System, including suitable transmitter, receiver, and amplifier. In some configurations, the RGB channels may be transformed into alternative orthogonal spaces such as HSL (hue, saturation, luminance). Additional examples of such inspection sensors 310 may include the Sick PS30 pattern sensor, Keyence AI series pattern matching sensor, Cognex Insight cameras, DVT Legend or Keyence smart cameras, component vision systems such as National Instruments PXI or PC based vision system such as Cognex VisionPro or any other vision system software which can run on a PC platform.

As discussed above, the print quality inspection system 308 may be configured to calculate a full print quality score that provides an objective representation of print quality of a printed region 400. The print quality inspection system 308 may utilize various sensors 310 to inspect the printed region 400 and communicate measurements and/or images to the analyzer 312. The analyzer 312 may then calculate one or more quality subscores based on respective measurements and/or images received from the sensors 310, and in turn, a full print quality score may be calculated based on one or more of the quality subscores. For example, as shown in FIG. 3, the print quality inspection system 308 may include a first sensor 310a, a second sensor 310b, and a third sensor 310c.

With continued reference to FIG. 3, the first sensor 310a may be configured as a first camera. In operation, the first sensor 310a may inspect the printed region and communicate an image of the printed region 400 to the analyzer 312. The analyzer 312 may then compare the received image with a target image to calculate a first quality subscore, also referred to herein as a visual quality score, based on an array of scores for the inspected printed region 400. The array of scores may generated by soliciting and recording human feedback based on human perceptions of sample printed regions. Each score of the array is correlated with at least one inspection parameter defined by a comparison of a sample image of a printed region and a target image. In some configurations, the at least one inspection parameter may be selected from the group consisting of: grayscale, color, shape, mismatch size, and mismatch location.

It is to be appreciated that human feedback and human perceptions used to generate the array may correspond with consumer feedback based on consumer perceptions. It is also to be appreciated that consumer feedback may include any kind of information provided by the consumer as end-user which is or may be relevant to print quality data. Consumer feedback may include, for example, responses to questionnaires or interviews, complaints made by dissatisfied customers, any of which may be recorded in written form, or as audio or video recording; and/or images of product in use or after use. Human feedback may also be transmitted directly from feedback providers to the analyzer in various ways, such as via written communication; electronic communication; internet interface; and/or combinations thereof. As such, human feedback can be communicated with various types of devices, such as telephones; computers; mobile devices such as mobile telephones; smart phones; tablets; and the like. Human feedback may also be transmitted in various ways from feedback providers to intermediaries, which can then communicate and/or enter the information parameters into the analyzer.

Referring still to FIG. 3, the second sensor 310b may be configured as a spectrophotometer. In operation, the second sensor 310b may inspect the printed region 400 and measure a delta E that is communicated to the analyzer 312. In turn, the analyzer 312 may calculate a second quality subscore, also referred to herein as a delta E score, based the delta E measurement. In some configurations, the delta E may be calculated based on L*, a*, b* values of the printed region (pr) relative to L*, a*, b* values of an unprinted region of the substrate (s) as follows:

$$\Delta E = [(L^*_{pr} - L^*_s)^2 + (a^*_{pr} - a^*_s)^2 + (b^*_{pr} - b^*_s)^2]^{1/2}$$

It is to be appreciated that the delta E may be calculated using various types of other methods and algorithms, such as for example, the "Delta E CMC" method and the "Delta E CIE 2000" method. In some configurations, the second sensor 310b may also inspect the printed region 400 to measure a dot area that is communicated to the analyzer 312. In turn, the analyzer 312 may calculate a third quality subscore, also referred to herein as a dot area score, based the dot area measurement.

As shown in FIG. 3, the third sensor 310c may be configured as a second camera. In operation, the third sensor may inspect the printed region 400 and measure a color to color registration that is communicated to the analyzer 312. In turn, the analyzer 312 may calculate a fourth quality subscore, also referred to herein as a color to color registration score, based the color to color registration measurement.

With reference to the above description, the analyzer 312 may calculate a full print quality score based on one or more quality subscores. For example, the full print quality score may be calculated based on the first print quality subscore. In some configurations, the full print quality score may be calculated based on the first print quality subscore and any one or more of the second quality subscore, the third quality subscore, and the fourth quality subscore. In turn, the analyzer 312 may then execute a control action based on the full print quality score.

Example Implementation

To provide additional context to the above discussion, the following provides a specific description of one example implementation of the processes herein that may be used to calculate a full print quality score that may correlate with an objective evaluation of the print quality of a printed region on a substrate. For the purposes of the present example, the full print quality score is scaled from 1 to 5, wherein a relatively high score represents a relatively good print quality and a relatively low score represents a relatively poor print quality. For example, a full print quality score of 5 may be considered perfect and a full print quality score of 1 may be considered failing. As discussed below, a first quality subscore, a second quality subscore, a third quality subscore, and a fourth quality subscore may be weighted and used to calculate the full print quality score. For the present example, each subscore may have a scale of 1 to 5 and may be equally weighted at 25% of the full print quality score.

As discussed above, the first quality subscore (visual quality score) may be calculated based on an array of scores. For example, Table 1 below provides an example array of scores, in the form of deductions, based on a mismatch size and a designated importance of the location of the mismatch on an assembled product. It is to be appreciated that the designated importance of a location on an assembled product may be defined in various ways. For example, an "important location" may represent a location on an assembled product that is readily visible to a consumer during product use. In another example, an "unimportant location" may represent a location on an assembled product that is not visible to a consumer during product use.

TABLE 1

| | Location of Mismatch on Product | | |
|---|---|---|---|
| Mismatch Size | Important Location | Mid-Important Location | Unimportant Location |
| Less than or equal to 3 mm | −2.00 | −1.50 | −1.00 |
| Greater than 3 mm and less than 10 mm | −2.00 | −1.50 | −1.00 |
| Greater than or equal to 10 mm | −4.00 | −3.00 | −2.00 |

In the present example, a first quality subscore may be calculated by adding a score (deduction) from the array in Table 1 to a score of 5.0. For example, if the inspected printed area has a mismatch size that is 5 mm long and the mismatch is located in an important location, the first quality subscore may be calculated as:

First Quality Subscore=5.00+(−2.00)=3.00

Continuing with the present example, a second quality subscore may be calculated based on the measured delta E. For example, Table 2 below provides a sample array of second subscores based on measured delta E values.

TABLE 2

| Measured Delta E at 100% | Score |
|---|---|
| 0.00 to 0.50 | 5.00 |
| 0.51 to 1.00 | 4.50 |
| 1.01 to 2.00 | 4.00 |
| 2.01 to 3.00 | 3.00 |
| 3.01 to 4.00 | 2.00 |
| 4.01 or greater | 1.00 |

As such, for example, using the values in Table 2 above, if the measured delta E is 1.80, then the second quality subscore is 4.00.

Continuing with the present example, a third quality subscore may be calculated based on the measured dot area. For example, Table 3 below provides a sample array of third quality subscores based on measured dot area values.

TABLE 3

| Dot Area Percentage From Target | Score |
|---|---|
| (+/−) 3.00% or less | 5.00 |
| (+/−) 4.00% | 4.00 |
| (+/−) 5.00% | 3.50 |
| (+/−) 6.00% | 3.25 |

TABLE 3-continued

| Dot Area Percentage From Target | Score |
|---|---|
| (+/−) 7.00% | 3.00 |
| (+/−) 8.00% | 2.00 |
| (+/−) 9.00% or more | 1.00 |

As such, for example, using the values in Table 3 above, if the measured dot area percentage is 3.0% from the target, then the third quality subscore is 5.00.

Continuing with the present example, a fourth quality subscore may be calculated based on the measured color to color registration. For example, Table 4 below provides a sample array of fourth quality subscores based on color-to-color registration values.

TABLE 4

| Color-to-Color Registration | Score |
|---|---|
| 0.0 mm | 5.00 |
| 0.01 mm to 0.05 mm | 4.00 |
| 0.06 mm to 0.10 mm | 3.00 |
| 0.11 mm to 0.25 mm | 2.00 |
| Greater than 0.25 mm | 1.00 |

As such, for example, using the values in Table 4 above, if the measured color-to-color registration is 0.05 mm, then the fourth quality subscore is 4.00

As discussed above, each subscore may also be weighted by a percentage before calculating the full print quality score. For the present example, each subscore may be weighted by 25%, and the full print quality score may be calculated by adding the weighted subscores together as shown in Table 5 below.

TABLE 5

| | Subscore Value | Weighted Subscore |
|---|---|---|
| First Quality Subscore | 3.00 | 0.75 |
| Second Quality Subscore | 4.00 | 1.00 |
| Third Quality Subscore | 5.00 | 1.25 |
| Fourth Quality Subscore | 4.00 | 1.00 |
| Full Print Quality Score | | 4.00 |

Thus, for the present example, the Full Print Quality Score is 4.00.

The above described example method and associated calculations utilizing the above described Quality Subscores 1-4 used to calculate a Full Print Quality Score are provided as one example implementation. It is to be appreciated that various different calculations may be utilized to generate various different combinations of Quality Subscores that may be utilized to calculate a Full Print Quality Score in different ways. In addition, although the above described Quality Subscores are based on visual quality; delta E; dot area; and color-to-color registration, it is to be appreciated that Quality Subscores may be based on various other parameters, such as for example, ink optical density; dot area at minimum dot; neutral gray; substrate color; substrate opacity (which may be measured by an in-line spectrophotometer); 1D barcodes; and/or barcodes.

This application claims the benefit of U.S. Provisional Application No. 62/666,122, filed on May 3, 2018, the entirety of which is incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assessing print quality, the method comprising steps of:
generating an array of scores by soliciting and recording human feedback based on human perceptions of sample printed regions, wherein each score is correlated with at least one inspection parameter defined by a comparison of a sample image of a printed region and a target image, wherein the at least one inspection parameter is selected from the group consisting of:
grayscale, color, shape, mismatch size, and mismatch location;
providing a communication network;
connecting a camera with the communication network;
connecting an analyzer with the communication network;
advancing a substrate in a machine direction,
depositing ink to the substrate to create a printed region;
inspecting the printed region with the camera;
communicating an image of the printed region from the camera to the analyzer;
comparing the image with the target image to calculate a visual quality score based on the array for the inspected printed region; and
executing a control action based on the visual quality score.

2. The method of claim 1, further comprising converting the substrate into discrete articles, wherein at least one discrete article comprises the printed region.

3. The method of claim 2, wherein the discrete articles are selected from the group consisting of: diapers, sanitary napkins, panty liners, bags, and boxes.

4. The method of claim 1, further comprising:
providing a spectrophotometer;
inspecting the printed region with the spectrophotometer to measure a delta E;
calculating a delta E score based on the measured delta E; and
calculating a full print quality score based on the delta E score and the visual quality score.

5. The method of claim 1, further comprising:
providing a spectrophotometer;
inspecting the printed region with the spectrophotometer to measure a dot area;
calculating a dot area score based on the measured dot area; and
calculating a full print quality score based on the dot area score and the visual quality score.

6. The method of claim 1, further comprising:
providing a second camera;
inspecting the printed region with the second camera to measure a color to color registration;
calculating a color to color registration score based on the measured color to color registration; and
calculating a full print quality score based on the color to color registration score.

7. The method of claim 1, wherein the control action comprises at least one of rejecting the substrate and providing a suggested corrective action.

8. The method of claim 1, wherein the substrate comprises at least one of a film, a nonwoven, and paper.

9. The method of claim 1, further comprising generating human feedback by soliciting and recording consumer feedback relating to consumer perceptions of sample printed regions.

10. The method of claim 1, wherein the step of depositing ink further comprises printing the printed region with at least one of flexographic printing, rotogravure printing, and digital printing.

11. A method for assessing print quality, the method comprising steps of:
generating an array of scores by soliciting and recording human feedback based on human perceptions of sample printed regions, wherein each score is correlated with at least one inspection parameter defined by a comparison of a sample image of a printed region and a target image, wherein the at least one inspection parameter is selected from the group consisting of:
grayscale, color, shape, mismatch size, and mismatch location;
providing a communication network;
connecting a camera and a spectrophotometer with the communication network;
connecting an analyzer with the communication network;
advancing a substrate in a machine direction, the substrate comprising a printed region;
inspecting the printed region with the camera;
communicating an image of the printed region from the camera to the analyzer;
comparing the image with the target image to calculate a first score based on the array for the inspected printed region; and
inspecting the printed region with the spectrophotometer to measure at least one of a delta E and a dot area;
calculating second score based on at least one of the measured delta E and dot area;
calculating a full print quality score based on the first score and the second score;
converting the substrate into discrete articles, wherein at least one discrete article comprises the printed region; and
executing a control action based on the full print quality score.

12. The method of claim 11, further comprising:
providing a spectrophotometer; and
inspecting the printed region with the spectrophotometer to measure the delta E and the dot area.

13. The method of claim 11, further comprising:
providing a second camera;
inspecting the printed region with the second camera to measure a color to color registration;
calculating a third score based on the measured color to color registration; and
wherein the full print quality score is further based on the third score.

14. The method of claim 11, wherein the control action comprises at least one of rejecting the at least one discrete article and providing a suggested corrective action.

15. The method of claim 11, wherein the discrete articles are selected from the group consisting of: diapers, sanitary napkins, panty liners, bags, and boxes.

16. The method of claim 11, wherein the substrate comprises at least one of a film, a nonwoven, and paper.

17. The method of claim 11, further comprising generating human feedback by soliciting and recording consumer feedback relating to consumer perceptions of sample printed regions.

18. The method of claim 11, further comprising printing the printed region with at least one of flexographic printing, rotogravure printing, and digital printing.

19. A method for assessing print quality, the method comprising steps of:
generating an array of scores by soliciting and recording consumer feedback based on consumer perceptions of sample printed regions, wherein each score is correlated with at least one inspection parameter defined by a comparison of a sample image of a printed region and a target image, wherein the at least one inspection parameter is selected from the group consisting of: grayscale, color, shape, mismatch size, and mismatch location;
providing a communication network;
connecting a first camera, a second camera, and a spectrophotometer with the communication network;
connecting an analyzer with the communication network;
advancing a substrate in a machine direction, the substrate comprising a printed region;
inspecting the printed region with the first camera;
communicating an image of the printed region from the camera to the analyzer;
comparing the image with the target image to calculate a first score based on the array for the inspected printed region; and
inspecting the printed region with the spectrophotometer to measure a delta E and a dot area;
calculating a second score based on the measured delta E;
calculating a third score based on the measured dot area;
inspecting the printed region with the second camera to measure a color to color registration;
calculating a fourth score based on the measured color to color registration;
calculating a full print quality score based on the first score, the second score, the third score, and the fourth score;
converting the substrate into discrete articles, wherein at least one discrete article comprises the printed region; and
executing a control action based on the full print quality score.

20. The method of claim 19, wherein the control action comprises at least one of rejecting the at least one discrete article and providing a suggested corrective action.

* * * * *